United States Patent [19]
Ulrich et al.

[11] Patent Number: 5,877,217
[45] Date of Patent: Mar. 2, 1999

[54] N-ACYLAMINOALKYL-HYDRAZINECARBOXIMIDAMIDES

[75] Inventors: Peter C. Ulrich, Old Tappan, N.J.; Dilip R. Wagle, Valley Cottage, N.Y.

[73] Assignee: Alteon Inc., Ramsey, N.J.

[21] Appl. No.: 771,959

[22] Filed: Dec. 23, 1996

Related U.S. Application Data

[60] Provisional application No. 60/009,220 Dec. 26, 1995.
[51] Int. Cl.$^6$ .......................... A61K 31/16; C07C 307/00
[52] U.S. Cl. ............................................. 514/614; 564/81
[58] Field of Search ............................................. 514/614

[56] References Cited

U.S. PATENT DOCUMENTS

| | | |
|---|---|---|
| 2,258,321 | 10/1941 | Ericks . |
| 2,289,541 | 7/1942 | Bricks et al. . |
| 2,300,570 | 11/1942 | Heuser et al. . |
| 2,375,659 | 5/1945 | Jones et al. . |
| 2,928,829 | 3/1960 | Mull . |
| 2,951,843 | 9/1960 | Haack et al. . |
| 3,006,913 | 10/1961 | Mull . |
| 3,053,732 | 9/1962 | Greenhalgh . |
| 3,055,882 | 9/1962 | Mull . |
| 3,055,883 | 9/1962 | Mull . |
| 3,081,222 | 3/1963 | Hagemann et al. . |
| 3,098,066 | 7/1963 | Mull . |
| 3,099,599 | 7/1963 | Copp et al. . |
| 3,101,336 | 8/1963 | James et al. . |
| 3,178,433 | 4/1965 | Mull . |
| 3,183,241 | 5/1965 | Oja . |
| 3,200,111 | 8/1965 | Paquette . |
| 3,201,459 | 8/1965 | Coda et al. . |
| 3,202,710 | 8/1965 | Bolger . |
| 3,283,003 | 11/1966 | Jack et al. . |
| 3,291,829 | 12/1966 | Mull . |
| 3,313,813 | 4/1967 | Cragoe, Jr. . |
| 3,317,545 | 5/1967 | Albrecht et al. . |
| 3,364,220 | 1/1968 | Biel et al. . |
| 3,506,680 | 4/1970 | Berger et al. . |
| 3,681,504 | 8/1972 | Johnston et al. . |
| 3,803,324 | 4/1974 | Winter et al. . |
| 3,978,060 | 8/1976 | Forsythe et al. . |
| 3,980,774 | 9/1976 | Hegarty et al. . |
| 3,991,209 | 11/1976 | Forsythe et al. . |
| 4,072,757 | 2/1978 | Okamoto et al. . |
| 4,161,541 | 7/1979 | Rasmussen . |
| 4,226,885 | 10/1980 | Orzalesi et al. . |

(List continued on next page.)

FOREIGN PATENT DOCUMENTS

| | | |
|---|---|---|
| 0 158 020 | 10/1985 | European Pat. Off. . |
| 0 222 313 | 11/1986 | European Pat. Off. . |
| 325936 | 1/1989 | European Pat. Off. . |
| 2059975 | 6/1971 | France . |
| 2029707 | 12/1970 | Germany . |
| 3040993 | 6/1982 | Germany . |
| 64-56614 | 8/1987 | Japan . |
| 63-287492 | 11/1988 | Japan . |
| 809165 | 5/1957 | United Kingdom . |
| 952194 | 12/1961 | United Kingdom . |
| 1036987 | of 1968 | United Kingdom . |
| 1274668 | 6/1968 | United Kingdom . |
| 1458636 | 9/1974 | United Kingdom . |

OTHER PUBLICATIONS

Acharya et al. 1988. Biochemistry 27(12):4522–9.
Brownlee et al. 1986. Science 232: 1629–32.
Brownlee et al. 1984. Ann. Int. Med. 101:527–37.
Brownlee et al. 1983. J. Exp. Med. 158: 1739–44.
Brownlee et al., Diabetes, 35, Suppl. 1, p. 42A (1986).
Bucala et al. (1992) In Advances in Pharmacology, vol. 23, pp. 1–34, Academic Press.
Bunn et al. 1975. Biochem. Biophys. Res. Comm. 67: 103–9.
Ebetino et al. 1962. J. Org. Chem. 27: 188–91.
Ebetino et al. 1964. *J. Org. Chem.* 29: 2582–5.
Eble et al., (1983), J. Biol. Chem., 258:9406–9412.
Finot. 1982. In *Food and Nutritional Aspects*. Feeney and Whitaker, eds. American Chemical Society 198: 91–124.
Geluk et al. (1969) Notes:712–5.
Godfrey. 1962. Doctoroal Dissertation. U. of London.
Hayase et al, J. Biol. Chem., 263, pp. 3758–3764 (1989).
Hollis et al. 1985. *Diabetologia* 28: 282–85.
Koenig et al. 1977. *J. Biol. Chem.* 252: 2992–7.
Kohn et al. 1984. Diabetes 33(1): 57–9.
Lindberg and Tornqvist. 1966. Acta Obst. Gynec. Scand 45: 131–9.
Maillard. C.R. Acad. Sci. 154: 66–8.
Monnier et al. 1984. Proc. Natl. Acad. Sci. 81: 583–7.
Monnier and Cerami. 1983. In Maillard Reaction in Food and Nutrition. Waller, ed. American Chemical Society 215: 431–49.
Stoner et al. 1985 Agents and Actions 17:5–9.
Sundberg et al. 1990. J. Med. Chem. 33: 298–307.
Tai et al. 1984. J. Med. Chem. 27: 236–8.
Wagenaar et al. (1993) J. Org. Chem. 58:4331–8.

(List continued on next page.)

*Primary Examiner*—Zohreh Fay
*Attorney, Agent, or Firm*—Klauber & Jackson

[57] ABSTRACT

The present invention relates to compositions and methods for inhibiting nonenzymatic cross-linking (protein aging) using compounds of the following formula I

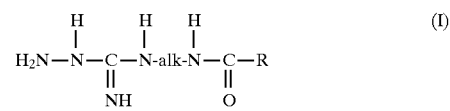

wherein alk is a straight or branched chain alkylene group containing from 2 to 8 carbon atoms, and R is a lower alkyl group containing from 1 to 6 carbon atoms; and their biologically or pharmaceutically acceptable acid addition salts. Accordingly, a compositions are disclosed which comprises these N-acylaminoalkylhydrazinecarboximidamides, which are capable of inhibiting the formation of advanced glycosylation endproducts of target proteins. The method comprises contacting the target protein with the composition. Both industrial and therapeutic applications for the invention are envisioned, as food spoilage and animal protein aging can be treated.

26 Claims, No Drawings

U.S. PATENT DOCUMENTS

| | | |
|---|---|---|
| 4,271,190 | 6/1981 | Bertelmann et al. . |
| 4,471,137 | 9/1984 | Barton et al. . |
| 4,544,759 | 10/1985 | Hlavaka et al. . |
| 4,665,192 | 5/1987 | Cerami et al. . |
| 4,680,300 | 7/1987 | Nelson et al. . |
| 4,731,383 | 3/1988 | Erczi et al. . |
| 4,758,531 | 7/1988 | Cerami et al. . |
| 4,758,583 | 7/1988 | Cerami et al. . |
| 4,908,446 | 3/1990 | Ulrich et al. . |
| 4,990,537 | 2/1991 | Okuyama et al. . |
| 5,006,523 | 4/1991 | Atwal . |
| 5,140,048 | 8/1992 | Ulrich et al. . |
| 5,189,046 | 2/1993 | Burch et al. . |
| 5,196,450 | 3/1993 | Sjoerdsma et al. . |
| 5,296,498 | 3/1994 | Malen et al. . |
| 5,336,689 | 8/1994 | Weber et al. . |

OTHER PUBLICATIONS

Monnier and Cerami. 1983. Biochem. Biophys. Acta. 760: 97–103.

Monnier and Cerami. 1982. Clin. Endocrinol. Metab. 11: 431–52.

Monnier and Cerami. 1981. Science 211: 491–3.

Murdock et al. 1982. J. Med. Chem. 25: 505–18.

Nakashima et al. (1987) Eur. J. Med. Chem. 22:553–8.

Nicholls et al., Lab. Invest., 60, No. 4, p. 486 (1989).

Nordbo, J. Dent. Res., 58, p. 1429 (1979).

Oimomi et al., Agric. Biol. Chem., 53(6):1727–1728 (1989).

Oimomi et al.Diabetes Research and Clinical Practice, 6:311–313 (1989).

Pongor et al. 1984. Proc. Natl. Acad. Sci. USA 81:2684–8.

Potekhin et al. 1973. Zhurn. Organiche. Khi. 9:1180–6 (English translation).

Rowland, G.F. (1977) Eur. J. Cancer 13:593–6.

Scofield et al. (1977) Anal. Biochem. 77:152–7.

Sell and Monnier, J. Biol. Chem. 264, pp. 21597–21602 (1989).

N-ACYLAMINOALKYL-HYDRAZINECARBOXIMIDAMIDES

This application claims priority from pending provisional application No. 60/009,220, filed Dec. 26, 1995.

BACKGROUND OF THE INVENTION

The present invention relates generally to the aging of proteins resulting from their reaction with glucose and other reducing sugars, and more particularly to the inhibition of the reaction of nonenzymatically glycosylated proteins and the often resultant formation of advanced glycosylation (glycation) endproducts and cross-links.

The reaction between glucose and proteins has been known for some time. Its earliest manifestation was in the appearance of brown pigments during the cooking of food, which was identified by Maillard in 1912, who observed that glucose or other reducing sugars react with amino acids to form adducts that undergo a series of dehydrations and rearrangements to form stable brown pigments. Further is studies have suggested that stored and heat treated foods undergo nonenzymatic browning as a result of the reaction between glucose and the polypeptide chain, and that the proteins are resultingly cross-linked and correspondingly exhibit decreased bioavailability.

This reaction between reducing sugars and food proteins was found to have its parallel in vivo. Thus, the nonenzymatic reaction between glucose and the free amino groups on proteins to form a stable, 1-deoxyketosyl adduct, known as the Amadori product, has been shown to occur with hemoglobin, wherein a rearrangement of the amino terminal of the beta-chain of hemoglobin by reaction with glucose, forms the adduct known as hemoglobin $A_{1c}$. The reaction has also been found to occur with a variety of other body proteins, such as lens crystallins, collagen and nerve proteins. See Bucala et al., "Advanced Glycosylation; Chemistry, Biology, and Implications for Diabetes and Aging" in *Advances in Pharmacology*, Vol. 23, pp. 1–34, Academic Press (1992). Moreover, brown pigments with spectral and fluorescent properties similar to those of late-stage Maillard products have also been observed in vivo in association with several long-lived proteins, such as lens proteins and collagen from aged individuals. An age-related linear increase in pigment was observed in human dura collagen between the ages of 20 to 90 years. Interestingly, the aging of collagen can be mimicked in vitro by the cross-linking induced by glucose; and the capture of other proteins and the formation of adducts by collagen, also noted, is theorized to occur by a cross-linking reaction, and is believed to account for the observed accumulation of albumin and antibodies in kidney basement membrane.

In U.S. Pat. No. 4,758,583, a method and associated agents were disclosed that served to inhibit the formation of advanced glycosylation endproducts by reacting with an early glycosylation product that results from the original reaction between the target protein and glucose. Accordingly, inhibition was postulated to take place as the reaction between the inhibitor and the early glycosylation product appeared to interrupt the subsequent reaction of the glycosylated protein with additional protein material to form the cross-linked late-stage product. One of the agents identified as an inhibitor was aminoguanidine, and the results of further testing have borne out its efficacy in this regard.

While the success that has been achieved with aminoguanidine and similar compounds is promising, a need continues to exist to identify and develop additional inhibitors that broaden the availability and perhaps the scope of this potential activity and its diagnostic and therapeutic utility.

SUMMARY OF THE INVENTION

In accordance with the present invention, a method and compositions are disclosed for the inhibition of the advanced glycosylation of proteins (protein aging). In particular, the compositions comprise agents for inhibiting nonenzymatic cross-linking (protein aging) due to the formation of advanced glycosylation (glycation) endproducts. The agents may be selected from those materials capable of reacting with an early glycosylation product from the reaction of glucose with proteins and preventing further reactions. Cross-linking caused by other reactive sugars present in vivo or in foodstuffs, including ribose, galactose and fructose would also be prevented by the methods and compositions of the present invention.

The agents comprise N-acylaminoalkylhydrazine-carboximidamides having the following structural formula:

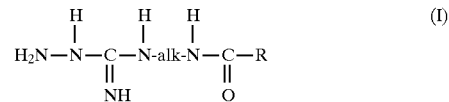

wherein alk is a straight or branched chain alkylene group containing from 2 to 8 carbon atoms, and R is a lower alkyl group containing from 1 to 6 carbon atoms; and their biologically or pharmaceutically acceptable acid addition salts; and mixtures thereof, and a carrier therefor.

The compounds, and their compositions, utilized in this invention appear to react with an early glycosylation product thereby preventing the same from later forming the advanced glycosylation end products which lead to protein cross-links, and thereby, to protein aging.

The present invention also relates to a method for inhibiting protein aging by contacting the initially glycosylated protein at the stage of the early glycosylation product with a quantity of one or more of the agents of the present invention, or a composition containing the same. In the instance where the present method has industrial application, one or more of the agents may be applied to the proteins in question, either by introduction into a mixture of the same in the instance of a protein extract, or by application or introduction into foodstuffs containing the protein or proteins, all to prevent premature aging and spoilage of the particular foodstuffs.

The ability to inhibit the formation of advanced glycosylation endproducts carries with it significant implications in all applications where protein aging is a serious detriment. Thus, in the area of food technology, the retardation of food spoilage would confer an obvious economic and social benefit by making certain foods of marginal stability less perishable and therefore more available for consumers. Spoilage would be reduced as would the expense of inspection, removal, and replacement, and the extended availability of the foods could aid in stabilizing their price in the marketplace. Similarly, in other industrial applications where the perishability of proteins is a problem, the admixture of the agents of the present invention in compositions containing such proteins would facilitate the extended useful life of the same. Presently used food preservatives and discoloration preventatives such as sulfur dioxide, known to cause toxicity including allergy and asthma in animals, can be replaced with compounds such as those described herein.

The present method has particular therapeutic application as the Maillard process acutely affects several of the significant protein masses in the body, among them collagen, elastin, lens proteins, and the kidney glomerular basement membranes. These proteins deteriorate both with age (hence the application of the term "protein aging") and as a consequence of diabetes. Accordingly, the ability to either retard or substantially inhibit the formation of advanced glycosylation endproducts carries the promise of treatment for diabetes and, of course, improving the quality and, perhaps, duration of animal life.

The present agents are also useful in the area of personal appearance and hygiene, as they prevent the staining of teeth by cationic anti-microbial agents with anti-plaque properties, such as chlorhexidine.

Accordingly, it is a principal object of the present invention to provide a method for inhibiting the extensive cross-linking of proteins that occurs as an ultimate consequence of the reaction of the proteins with glucose and other reactive sugars, by correspondingly inhibiting the formation of advanced glycosylation endproducts.

It is a further object of the present invention to provide a method as aforesaid which is characterized by a reaction with an initially glycosylated protein identified as an early glycosylation product.

It is a further object of the present invention to provide a method as aforesaid which prevents the rearrangement and cross-linking of the said early glycosylation products to form the said advanced glycosylation endproducts.

It is a yet further object of the present invention to provide agents capable of participating in the reaction with the said early glycosylation products in the method as aforesaid.

It is a still further object of the present invention to provide therapeutic methods of treating the adverse consequences of protein aging by resort to the aforesaid method and agents.

It is a still further object of the present invention to provide a method of inhibiting the discoloration of teeth by resort to the aforesaid method and agents.

It is a still further object of the present invention to provide compositions including pharmaceutical compositions, all incorporating the agents of the present invention.

It is still further object of the present invention to provide novel compounds, as well as processes for their preparation, for use in the methods and compositions of the present invention.

Other objects and advantages will become apparent to those skilled in the art from a consideration of the ensuing description.

DETAILED DESCRIPTION OF THE PREFERRED EMBODIMENT

In accordance with the present invention, agents, compositions including pharmaceutical compositions containing said agents and associated methods been developed which are believed to inhibit the formation of advanced glycosylation endproducts in a number of target proteins existing in both animal and plant material. In particular, the invention relates to a composition which may contain one or more agents comprising N-acylaminoalkylhydrazinecarboximidamides having the structural formula:

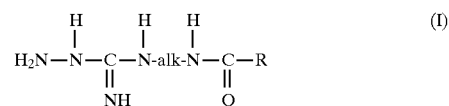

wherein alk is a straight or branched chain alkylene group containing from 2 to 8 carbon atoms, and R is a lower alkyl group containing from 1 to 6 carbon atoms; and their biologically or pharmaceutically acceptable acid addition salts; and mixtures thereof, and a carrier therefor.

The lower alkyl groups referred to above preferably contain 1–6 carbon atoms and include methyl, ethyl, propyl, butyl, pentyl, hexyl, and the corresponding branched-chain isomers thereof. These groups are optionally substituted by one or more halo, hydroxy, amino or lower alkylamino groups.

The alkylene groups referred to herein contain from 2 to 8 carbon atoms and likewise can be straight or branched chain, and are thus exemplified by ethylene, propylene, butylene, pentylene, hexylene, heptylene, octylene, and their corresponding branched chain isomers.

The halo atoms in the above formula may be fluoro, chloro, bromo or iodo. The lower alkoxy groups contain 1–6, and preferably 1–3, carbon atoms and are illustrated by methoxy, ethoxy, n-propoxy, isopropoxy and the like.

For the purposes of this invention equivalent to the compounds of formula (I) are the biologically and pharmaceutically acceptable acid addition salts thereof. Such acid addition salts may be derived from a variety of organic and inorganic acids such as sulfuric, phosphoric, hydrochloric, hydrobromic, sulfamic, citric, lactic, maleic, succinic, tartaric, cinnamic, acetic, benzoic, gluconic, ascorbic, methanesulfonic and related acids.

Of the compounds encompassed by Formula I, certain substituents are preferred. For instance, the compounds wherein alk is an ethylene group and R is a methyl group are preferred. In particular, the novel compound which is N-(2-acetamidoethyl)hydrazinecarboximidamide hydrochloride or hydrobromide exhibits a profile of activity which is particularly useful for the treatment of mammalian, especially human, patients.

Representative compounds of the present invention include:

N-(2-acetamidoethyl)hydrazinecarboximidamide hydrobromide;

N-(2-acetamidoethyl)hydrazinecarboximidamide hydrochloride;

N-(3-acetamidopropyl)hydrazinecarboximidamide hydrobromide; and

N-(4-acetamidobutyl)hydrazinecarboximidamide hydrobromide.

The above compounds are capable of inhibiting the formation of advanced glycosylation endproducts on target proteins. The cross-linking of the protein to form the advanced glycosylation endproduct contributes to the entrapment of other proteins and results in the development in vivo of conditions such as reduced elasticity and wrinkling of the skin, certain kidney diseases, atherosclerosis, osteoarthritis and the like. Similarly, plant material that undergoes nonenzymatic browning deteriorates and, in the case of foodstuffs, become spoiled or toughened and, consequently, inedible. Thus, the compounds employed in accordance with this invention inhibit this late-stage Maillard effect and intervene in the deleterious changes described above.

The rationale of the present invention is to use agents which block the post-glycosylation step, i.e., the formation of fluorescent chromophores, the presence of which chromophores is associated with, and leads to adverse sequelae of diabetes and aging. An ideal agent would prevent the formation of the chromophore and its associate cross-links of proteins to proteins and trapping of proteins on the other proteins, such as occurs in arteries and in the kidney.

The chemical nature of the early glycosylation products with which the compounds of the present invention are believed to react may vary, and accordingly the term "early glycosylation product(s)" as used herein is intended to include any and all such variations within its scope. For example, early glycosylation products with carbonyl moieties that are involved in the formation of advanced glycosylation endproducts, and that may be blocked by reaction with the compounds of the present invention, have been postulated. In one embodiment, it is envisioned that the early glycosylation product may comprise the reactive carbonyl moieties of Amadori products or their further condensation, dehydration and/or rearrangement products, which may condense to form advanced glycosylation endproducts. In another scenario, reactive carbonyl compounds, containing one or more carbonyl moieties (such as glycolaldehyde, glyceraldehyde or 3-deoxyglucosone) may form from the cleavage of Amadori or other early glycosylation endproducts, and by subsequent reactions with an amine or Amadori product, may form carbonyl containing advanced glycosylation products such as alkylformyl-glycosylpyrroles.

Several investigators have studied the mechanism of advanced glycosylation product formation. In vitro studies by Eble et al., (1983), "Nonenzymatic Glucosylation and Glucose-dependent Cross-linking of Protein", *J. Biol. Chem.*, 258:9406–9412, concerned the cross-linking of glycosylated protein with nonglycosylated protein in the absence of glucose. Eble et al. sought to elucidate the mechanism of the Maillard reaction and accordingly conducted controlled initial glycosylation of RNAase as a model system, which was then examined under varying conditions. In one aspect, the glycosylated protein material was isolated and placed in a glucose-free environment and thereby observed to determine the extent of cross-linking.

Eble et al. thereby observed that cross-linking continued to occur not only with the glycosylated protein but with non-glycosylated proteins as well. One of the observations noted by Eble et al. was that the reaction between glycosylated protein and the protein material appeared to occur at the location on the protein chain of the amino acid lysine. Confirmatory experimentation conducted by Eble et al. in this connection demonstrated that free lysine would compete with the lysine on RNAase for the binding of glycosylated protein. Thus, it might be inferred from these data that lysine may serve as an inhibitor of advanced glycosylation; however, this conclusion and the underlying observations leading to it should be taken in the relatively limited context of the model system prepared and examined by Eble et al. Clearly, Eble et al. does not appreciate, nor is there a suggestion therein, of the discoveries that underlie the present invention, with respect to the inhibition of advanced glycosylation of proteins both in vitro and in vivo.

The experiments of Eble et al. do not suggest the reactive cleavage product mechanism or any other mechanism in the in vivo formation of advanced glycosylation endproducts in which glucose is always present. In fact, other investigators support this mechanism to explain the formation of advanced glycosylated endproducts in vivo (see for example Hayase et al, *J. Biol. Chem.*, 263, pp. 3758–3764 (1989); Sell and Monnier, *J. Biol. Chem.* 264, pp. 21597–21602 (1989) Oimomi et al., *Agric. Biol. Chem.*, 53(6):1727–1728 (1989); and *Diabetes Research and Clinical Practice*, 6:311–313 (1989). Accordingly, the use of lysine as an inhibitor in the Eble et al. model system has no bearing upon the utility of the compounds of the present invention in the inhibition of advanced glycosylated endproducts formation in the presence of glucose in vivo, and the amelioration of complications of diabetes and aging.

The compositions useful in the present invention comprise or contain agents capable of reacting with the active carbonyl intermediate of an early glycosylation product. Suitable agents are the compounds of Formula I of the present invention.

The present invention likewise relates to methods for inhibiting the formation of advanced glycosylation endproducts, which comprise contacting the target proteins with a composition of the present invention. In the instance where the target proteins are contained in foodstuffs, whether of plant or animal origin, these foodstuffs could have applied to them by various conventional means a composition containing the present agents.

In the food industry, sulfites were found years ago to inhibit the Maillard reaction and are commonly used in processed and stored foods. Recently, however, sulfites in food have been implicated in severe and even fatal reactions in asthmatics. As a consequence, the sulfite treatment of fresh fruits and vegetables has been banned. The mechanism for the allergic reaction is not known. Accordingly, the present compositions and agents offer a nontoxic alternative to sulfites in the treatment of foods in this manner.

As is apparent from a discussion of the environment of the present invention, the present methods and compositions hold the promise for arresting the aging of key proteins both in animals and plants, and concomitantly, conferring both economic and medical benefits as a result thereof. In the instance of foodstuffs, the administration of the present composition holds the promise for retarding food spoilage thereby making foodstuffs of increased shelf life and greater availability to consumers. Replacement of currently-used preservatives, such as sulfur dioxide known to cause allergies and asthma in humans, with non-toxic, biocompatible compounds is a further advantage of the present invention.

The therapeutic implications of the present invention relate to the arrest of the aging process which has, as indicated earlier, been identified in the aging of key proteins by advanced glycosylation and cross-linking. Thus, body proteins, and particularly structural body proteins, such as collagen, elastin, lens proteins, nerve proteins, kidney glomerular basement membranes and other extravascular matrix components would all benefit in their longevity and operation from the practice of the present invention. The present invention thus reduces the incidence of pathologies involving the entrapment of proteins by cross-linked target proteins, such as retinopathy, cataracts, diabetic kidney disease, glomerulosclerosis, peripheral vascular disease, arteriosclerosis obliterans, peripheral neuropathy, stroke, hypertension, atherosclerosis, osteoarthritis, periarticular rigidity, loss of elasticity and wrinkling of skin, stiffening of joints, glomerulonephritis, etc. Likewise, all of these conditions are in evidence in patients afflicted with diabetes mellitus. Thus, the present therapeutic method is relevant to treatment of the noted conditions in patients either of advanced age or those suffering from one of the mentioned pathologies.

Protein cross-linking through advanced glycosylation product formation can decrease solubility of structural proteins such as collagen in vessel walls and can also trap serum proteins, such as lipoproteins to the collagen. Also, this may result in increased permeability of the endothelium and consequently covalent trapping of extravasated plasma proteins in subendothelial matrix, and reduction in susceptibility of both plasma and matrix proteins to physiologic degradation by enzymes. For these reasons, the progressive occlusion of diabetic vessels induced by chronic hyperglycemia has been hypothesized to result from excessive formation of glucose-derived cross-links. Such diabetic microvascular changes and microvascular occlusion can be effectively prevented by chemical inhibition of advanced glycosylation product formation utilizing a composition and the methods of the present invention.

Studies indicate that the development of chronic diabetic damage in target organs is primarily linked to hyperglycemia so that tight metabolic control would delay or even prevent end-organ damage. See Nicholls et al., *Lab. Invest.,* 60, No. 4, p. 486 (1989), which discusses the effects of islet isografting and aminoguanidine in murine diabetic nephropathy. These studies further evidence that aminoguanidine diminishes aortic wall protein cross-linking in diabetic rats and confirm earlier studies by Brownlee et al., *Science,* 232, pp. 1629–1632 (1986) to this additional target organ of complication of diabetes. Also, an additional study showed the reduction of immunoglobulin trapping in the kidney by aminoguanidine (Brownlee et al., *Diabetes,* 35, Suppl. 1, p. 42A (1986)).

Further evidence in the streptozotocin-diabetic rat model that aminoguanidine administration intervenes in the development of diabetic nephropathy was presented by Brownlee et al., 1988, supra, with regard to morphologic changes in the kidney which are hallmarks of diabetic renal disease. These investigators reported that the increased glomerular basement membrane thickness, a major structural abnormality characteristic of diabetic renal disease, was prevented with aminoguanidine.

Taken together, these data strongly suggest that inhibition of the formation of advanced glycosylation endproducts (AGEs), by the teaching of the present invention, may prevent late, as well as early, structural lesions due to diabetes, as well as changes during aging caused by the formation of AGEs.

Diabetes-induced changes in the deformability of red blood cells, leading to more rigid cell membranes, is another manifestation of cross-linking and aminoguanidine has been shown to prevent it in vivo. In such studies, New Zealand White rabbits, with induced, long-term diabetes are used to study the effects of a test compound on red blood cell (RBC) deformability (df). The test compound is administered at a rate of 100 mg/kg by oral gavage to diabetic rabbits.

A further consequence of diabetes is the hyperglycemia-induced matrix bone differentiation resulting in decreased bone formation usually associated with chronic diabetes. In animal models, diabetes reduces matrix-induced bone differentiation by 70%.

Aminoguanidine, although a promising therapeutic agent, exhibits other pharmacological activities which, in certain circumstances, may limit its therapeutic usefulness in certain patient populations. Thus, the search has continued for an inhibitor of the formation of advanced glycosylation endproducts which is selective for this activity without significant effects on the enzymes diamino oxidase (DAO) and the inducible form of nitric oxide synthase (iNOS). The instant invention identifies the novel compound N-(2-acetamidoethyl)hydrazinecarboximidamide and its various salt forms, especially the hydrochloride, as uniquely being a selective inhibitor of the formation of advanced glycosylation endproducts without appreciable effects upon the diamino oxidase enzyme or nitric oxide formation. Thus, the present invention provides both methods and compositions for the inhibition of the formation of advanced glycosylation endproducts without concomitant inhibition of diamino oxidase and nitric oxide formation which comprise N-(2-acetamidoethyl)hydrazinecarboximidamide and its various salt forms.

In the instance where the compositions of the present invention are utilized for in vivo or therapeutic purposes, it may be noted that the compounds or agents used therein are biocompatible. Pharmaceutical compositions may be prepared with a therapeutically effective quantity of the agents or compounds of the present invention and may include a pharmaceutically acceptable carrier, selected from known materials utilized for this purpose. Such compositions may be prepared in a variety of forms, depending on the method of administration. Also, various pharmaceutically acceptable addition salts of the compounds of Formula I may be utilized.

A liquid form would be utilized in the instance where administration is by intravenous, intramuscular or intraperitoneal injection. When appropriate, solid dosage forms such as tablets, capsules, or liquid dosage formulations such as solutions and suspensions, etc., may be prepared for oral administration. For topical or dermal application to the skin or eye, a solution, a lotion or ointment may be formulated with the agent in a suitable vehicle such as water, ethanol, propylene glycol, perhaps including a carrier to aid in penetration into the skin or eye. For example, a topical preparation could include up to about 10% of the compound of Formula I. Other suitable forms for administration to other body tissues are also contemplated.

In the instance where the present method has therapeutic application, the animal host intended for treatment may have administered to it a quantity of one or more of the agents, in a suitable pharmaceutical form. Administration may be accomplished by known techniques, such as oral, topical and parenteral techniques such as intradermal, subcutaneous, intravenous or intraperitoneal injection, as well as by other conventional means. Administration of the agents may take place over an extended period of time at a dosage level of, for example, up to about 30 mg/kg.

As noted earlier, the invention also extends to a method of inhibiting the discoloration of teeth resulting from nonenzymatic browning in the oral cavity which comprises administration to a subject in need of such therapy an amount effective to inhibit the formation of advanced glycosylation endproducts of a composition comprising an agent of structural Formula I.

The nonenzymatic browning reaction which occurs in the oral cavity results in the discoloration of teeth. Presently used anti-plaque agents accelerate this nonenzymatic browning reaction and further the staining of the teeth. Recently, a class of cationic anti-microbial agents with remarkable anti-plaque properties have been formulated in oral rinses for regular use to kill bacteria in the mouth. These agents, the cationic antiseptics, include such agents as alexidine, cetyl pyridinium chloride, chlorhexidine gluconate, hexetidine, and benzalkonium chloride.

Tooth staining by chlorhexidine and other anti-plaque agents apparently results from the enhancement of the Maillard reaction. Nordbo, *J. Dent. Res.,* 58, p. 1429 (1979) reported that chlorhexidine and benzalkonium chloride catalyze browning reactions in vitro. Chlorhexidine added to mixtures containing a sugar derivative and a source of amino groups underwent increased color formation, attributed to the Maillard reaction. It is also known that use of chlorhexidine results in an increased dental pellicle. Nordbo proposed that chlorhexidine resulted in tooth staining in two ways: first, by increasing formation of pellicle which contains more amino groups, and secondly, by catalysis of the Maillard reaction leading to colored products.

In accordance with this method, the compounds of Formula I are formulated into compositions adapted for use in the oral cavity. Particularly suitable formulations are oral rinses and toothpastes incorporating the active agent.

In the practice of this invention, conventional formulating techniques are utilized with nontoxic, pharmaceutically acceptable carriers typically utilized in the amounts and combinations that are well-known for the formulation of such oral rinses and toothpastes.

The agent of Formula I is formulated in compositions in an amount effective to inhibit the formation of advanced glycosylation endproducts. This amount will, of course, vary with the particular agent being utilized and the particular dosage form, but typically is in the range of 0.01% to 1.0%, by weight, of the particular formulation.

Certain of the compounds encompassed by Formula I are novel compounds which can be prepared by modifications of chemical syntheses well-known in the art.

The compounds of formula I can be prepared according to the methods described in Nakashima et al., Eur. J. Med. Chem., 22 553–558 (1987). This reference describes, at page 554, the preparation of the hydrochloride salts of two compounds of formula I, i.e., N-(3-acetamidopropyl) hydrazinecarboximidamide (also known as 1-amino-3-acetamidopropylguanidine); and N-(4-acetamidobutyl) hydrazinecarboximidamide (also known as (1-amino-3-acetamidobutylguanidine).

One method of synthesis for the compounds of the instant invention is as shown in Scheme I below.

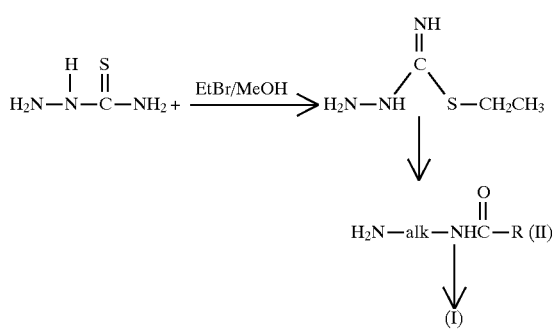

In this reaction scheme, thiosemicarbazide, dissolved in methanol, or another suitable polar solvent, is reacted with ethyl bromide and heated to reflux temperatures for a period of about 2 to 12 hours. Cooling to ambient temperatures and addition of t-butylmethyl ether to the methanolic solution resulted in precipitation of the S-ethylthiosemicarbazide hydrobromide.

Then, to the S-ethylthiosemicarbazide hydrobromide is added the appropriate N-acylalkylenediamine of formula II. After heating to reflux temperatures for a period of about 2 to 12 hours, and cooling, the desired N-acylaminoalkylhydrazinecarboxinidamide of formula I is isolated, and, if desired, purified by recrystallization from a suitable solvent such as a mixture of isopropanol and t-butylmethyl ether.

The various acid addition salts of the compounds of formula I are typically prepared from the corresponding hydrobromide by neutralization of the hydrobromide with a strong base, such as sodium hydroxide, followed by treatment with a strong acid to give the corresponding salt. Alternatively, the hydrobromide salt can be dissolved in methanol, and treated with gaseous hydrogen chloride to afford the corresponding hydrochloride salt.

A further method of preparing the compounds of the instant invention involves their preparation as shown in the Scheme II below:

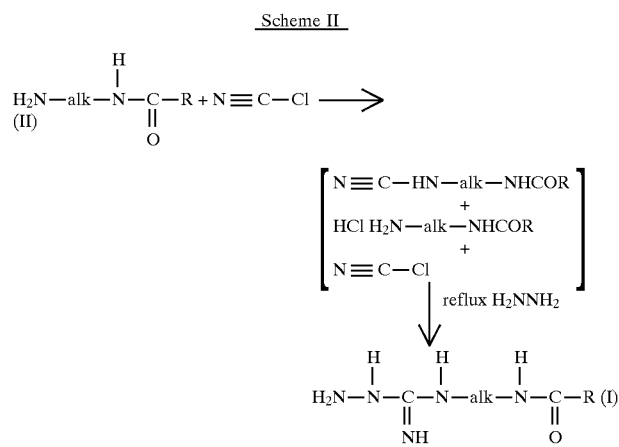

In this reaction Scheme II, cyanogen chloride is reacted with the appropriate N-acylalkylenediamine of formula II to afford a mixture of unisolated intermediates. These unisolated intermediates, shown in the reaction Scheme II above in the square brackets, are then refluxed with anyhydrous hydrazine in a polar solvent for a period of about 1 to about 15 hours.

Suitable polar solvents include alcohols such as 2-propanol and ethanol. The reaction temperature for the hydrazine addition step will, of course, depend upon, and vary with, the nature of the particular solvent chosen.

The following examples are illustrative of the invention.

EXAMPLE 1

A. S-Ethylthiosemicarbazide hydrobromide

Thiosemicarbazide (218.4 g, 2.4 mol) was taken up in ethanol (IL). To the mixture was added ethyl bromide (306.6 g, 2.8 mol) and the mixture was slowly heated to reflux. As the reaction proceeded, all solids dissolved into solution in 7 hours. The solution was refluxed for two more hours and was cooled to the ambient temperature. tert-Butylmethyl ether (700 mL) was added to the ethanolic solution and kept in the refrigerator overnight. White crystals were collected in two crops (418 g, 87%); mp 123–5° C. $^1$H-NMR($D_2O$) 3.18 (2H, dd), 1.39 (3H, t). $^{13}$C-NMR ($D_2O$) 169.6, 25.7, 13.8 ppm.

B. N-(2-acetamidoethyl)hydrazine carboxmidamide hydrobromide

To a solution of S-ethylthiosemicarbazide hydrobromide (100 g, 0.5 mol) in 750 mL of ethanol was added N-acetyl-ethylenediamine (51 g, 0.5 mol). The mixture was refluxed for 8 hours under the system connected to four bleach traps. Upon cooling the mixture, a white crystal formed and was filtered off. The solution was evaporated to a red oil under a vaccum system connected to bleach traps. The oil slowly crystalized in 2-propanol/tBuOMe to give white crystals (39.5 g, 33 %) of the title compound in three crops; mp 127–8° C. $^1$H-NMR ($D_2O$) 3.36 (4H, t), 2.00 (3H, S). $^{13}$C-NMR ($D_2O$) 175.0, 158.4, 40.6, 38.5, 22.3 ppm.

EXAMPLE 2

N-(2-acetamidoethyl)hydrazine carboxidamide hydrochloride

N-(2-acetamidoethyl)hydrazine carboximidamide hydrobromide (5 g, 20.8 mmol) was dissolved in 50 mL of water. Amberlite IRA-400 (OH) (50 g from Aldrich) was loaded on a column (2.5 cm dia.×45 cm) with a fritted glass. The resin was eluted with 200 mL of 1N NaOH and then with distilled water until pH 7. The aqueous hydrobromide solution was loaded on the resin and eluted dropwise. More water was eluted until the eluant became neutral. All aqueous fractions with positive ninhydrin test were combined and 10 mL of 6N HCl was added. Water was removed in vacuo to give a colorless oil, which subsequently was recrytallized from 2-propanol to yield 3.82 g (94%); mp 127–8 ° C. $^1$H-NMR ($D_2O$) 3.36 (4H, dt), 1.99 (3H, s). $^{13}$C-NMR ($D_2O$) 174.9, 158.2, 40.5, 38.4, 22.0 ppm.

EXAMPLE 3

N-(2-acetamidoethyl)hydrazine carboximidamide hydrochloride

The hydrobromide salt N-(2-acetamidoethyl)hydrazine carboximidamide hydrobromide (5 g, 20.8 mmol) was dissolved in 100 mL of methanol. To the stirred solution was passed HCl gas for 15 minutes in an ice bath. After passing HCl gas, the solution was stirred for 2 hours at room temperature and 200 mL of tBuOMe was added. After 24 hours, an oil seperated on the bottom of the flask. The liquid was decanted from the oil. The oil crystallized from 2-propanol/tBuOMe to give 3.3 g (82%) of white crystals which has the same physical properties with crystals from Method A.

EXAMPLE 4

In reaction sequence essentially as described in paragraphs A and B of Example 1, the appropriate starting materials are utilized to prepare the following compounds of formula I:

N-(3-acetamidopropyl)hydrazinecarboximidamide hydrobromide; and

N-(4-acetamidobutyl)hydrazinecarboximidamide hydrobromide.

EXAMPLE 5

N-(2-acetamidoethyl)hydrazinecarboximidamide hydrochloride

The following process must be carried out in a well-ventilated hood. An outlet of a 2 L three-neck flask, whose weight was earlier measured, is connected to a 6N KOH trap and the whole flask is cooled to –70° C. by immersing in a dry ice-acetone bath. To the flask is purged cyanogen chloride gas from a lecture bottle whose weight change was monitored on a balance. Sixty-two grams of cyanogen chloride (1 mol) is collected. To the liquified gas is then added cold 2-propanol (500 mL) and a mechanical stirrer apparatus. With vigorous stirring, a solution of N-acethylethylenediamine (102 g, 1 mol) in 2-propanol (500 mL) is added dropwise such that the internal temperature does not exceed 5° C. After addition is completed, the mixture is stirred for an hour at 5° C. and anhydrous hydrazine (28.2 mL, 0.9 mol) is added slowly. The mixture is stirred for an hour at 5° C., an additional hour at room temperature, and then refluxed for a further 15 hours. During the last hour of reflux, the volume of the reaction mixture is reduced by half by distillation removal of the solvent. Upon cooling, white cubic crystals slowly form. Crystals are then collected and dried to give the title compound.

EXAMPLE 6

The following method was used to evaluate the ability of the compounds of the present invention to inhibit the cross-linking of glycated bovine serum albumin (AGE-BSA) to the rat tail tendon collagen coated 96-well plate.

The AGE-BSA was prepared by incubating BSA at a concentration of 200 mg per ml with 200 mM glucose in 0.4M sodium phosphate buffer, pH 7.4 at 37° C. for 12 weeks. The glycated BSA was then extensively dialyzed against phosphate buffer solution (PAS) for 48 hours with additional 5 times buffer exchanges. The rat tail tendon collagen coated plate was blocked first with 300 µl of superbloc blocking buffer (Pierce #37515X) for one hour. The blocking solution was removed from the wells by washing the plate twice with PAS-Tween 20 solution (0.05 % Tween 20) using a NUNC-multiprobe or Dynatech ELISA-plate washer. Cross-linking of AGE-BSA (1 to 10 µg per well depending on the batch of AGE-BSA) to rat tail tendon collagen coated plate was performed with and without the testing compound dissolved in PAS buffer at pH 7.4 at the desired concentrations by the addition of 50 µl each of the AGE-BSA diluted in PAS or in the testing compound at 37° C. for 4 hours. The unbrowned BSA in PAS buffer with or without testing compound were added to the separate wells as the blanks. The uncross-linked AGE-BSA was then removed by washing the wells three times with PAS-Tween buffer. The cross-linked AGE-BSA to the tail tendon coated plate was then quantitated by the polyclonal antibody raised against AGE-RNase. After a one-hour incubation period, AGE antibody was removed by washing 4 times with PAS-Tween.

The bound AGE antibody was then detected with the addition of horseradish peroxidase-conjugated secondary antibody, e.g., goat anti-rabbit immunoglobulin and incubation for 30 minutes. The substrate of 2,2-azino-di(3-ethylbenzthiazoline sulfonic acid) (ABTS chromogen) (Zymed #00-2011) was added. The reaction was allowed for an additional 15 minutes and the absorbance was read at 410 nm in a Dynatech plate reader.

The % inhibition of each test compound was calculated as follows.

% inhibition={[Optical density (without compound) - optical density (with compound)]/optical density (without compound)]} 100%

The $IC_{50}$ relative inhibition by various test compounds at 10 mM is as follows:

| Test Compound | $IC_{50}$ |
|---|---|
| N-(2-acetamidoethyl)hydrazine-carboximidamide hydrobromide | 2.6 mM |
| N-(2-acetamidoethyl)hydrazine-carboximidamide hydrochloride | 3.6 mM |
| N-(3-acetamidopropyl)hydrazine-carboximidamide hydrobromide | 12.2 mM |
| Aminoguanidine hydrochloride | 12.0 mM |

The above experiment suggests that the compounds of formula I are more potent inhibitors of the formation of advanced glycosylation so that this type of drug therapy has benefits in reducing the pathology associated with the advanced glycosylation of proteins and the formation of cross-links between proteins and other macromolecules. Drug therapy may be used to prevent the increased trapping and cross-linking of proteins that occurs in diabetes and aging which leads to sequelae such as retinal damage, and extra-vascularly, damage to tendons, ligaments and other joints.

EXAMPLE 7

The following method was used to evaluate the ability of the compounds of the present invention to inhibit the cross-linking of N-acetyl glycyl-lysine methyl ester in the presence of ribose.

Materials:
N-acetylglycyllysine methyl ester (DP in formula below)
Ribose (R in formula below)
Test compounds (C in formula below)
Reagents:
0.5M sodium phosphate buffer pH 7.4
N-acetylglycyllysine methyl ester in 0.5M sodium phosphate buffer, pH 7.4
Ribose: 800 mM
Test compounds dissolved in the above buffer and the pH is adjusted to 7.4, if necessary
Procedure:
Reaction mixtures are prepared as follows:

| 80 mg/ml N-acetylglycyllysine methyl ester/buffer | 0.1 | 0.1 | — |
|---|---|---|---|
| ribose | 0.1 | 0.1 | 0.1 |
| test compound | — | 0.1 | 0.1 |
| buffer | 0.2 | 0.1 | 0.2 | and incubated at 37° C. for 16–24 hours. At the end of the incubation period, the fluorescence is read using an excitation wavelength of 350 nm and emission wavelength of 400 nm. The inhibition of the cross-linking is calculated from the decrease in the fluorescence in the presence of the test compounds according to the formula:

Inhibition (%)100×[DPRC fluorescence - RC fluorescence]/DPR fluorescence

The Inhibition by various test compounds ($IC_{50}$) is as follows:

| Test compound | $IC_{50}$mM |
|---|---|
| N-(2-acetamidoethyl)hydrazine-carboximidamide hydrobromide | 11.46 |
| N-(2-acetamidoethyl)hydrazine-carboximidamide hydrochloride | 10.64 |
| N-(3-acetamidopropyl)hydrazine-carboximidamide hydrochloride | >10.0 |
| Aminoguanidine hydrochloride | 10.0 |

The above experiment suggests that the compounds of formula I possess inhibitory activity in the formation of advanced glycosylation endproducts and this type of drug therapy will reduce the pathology associated with the advanced glycosylation of proteins and the formation of cross-links between proteins and other macromolecules. Drug therapy may be used to prevent the increased trapping and cross-linking of proteins that occurs in diabetes and aging which leads to sequelae such as retinal damage, and extra-vascularly, damage to tendons, ligaments and other joints.

EXAMPLE 8

To determine the effects of test compounds on the enzyme diamino oxidase the following assay procedure is utilized. This assay is a colorimetric kinetic enzyme assay based on the coversion of amine substrate to the corresponding aldehyde product which then reacts with reagent. The concentrations of enzyme and substrate used in this procedure ensure the reaction is at saturating conditions and linear for the time of incubation at room temperature.

Materials:
sodium phosphate buffer, 0.1M, pH=7.4
putrescine (Sigma), 0.03M (4.8 mg/ml)
diamine oxidase (Sigma), 3 U/ml (50 mg/ml)
o-aminobenzaldehyde (Sigma), (0.5 mg/ml)
96-well plate, plate reader w/absorbance filter at 450 nm
Procedure The reaction is conducted at room temperature. All reaction reagents and test compound dilution should be made up fresh in buffer, with the exception of the sodium phosphate buffer which can be stored at 4° C. for one month. Once prepared, the solutions can be maintained at room temperature. Putrescine and diamine oxidase are readily soluble in buffer. The o-aminobenzaldehyde (o-bzld) is light sensitive and requires slight heating at 37° C. This is done in a tube covered with alumninum foil. In addition, this reagent will begin to lose its activity following opening of the container due to oxidation so that it is necessary to work quickly with it. After warming up the container to room temperature, weigh out the necessary amount.

1. Pipet appropriate volumne of buffer to each well.
2. Add 50 μl of test compound to the appropriate wells. Add 50 μl of diamino oxidase (DAO) enzyme solution to the test and total wells. Allow the compound to interact with the enzyme for a fifteen minute pre-incubation step.
3. Blank the spectrophotometer to air. With a repeating pipetor, add 50 μl of the o-aminobenzaldehyde solution to all the wells. Afterwards, add 50 μl of the putrescine substate solution to the test and total wells. Substrate is not added to the blank wells. The initail absorbance is read at 450 nm in the automatic plate reater. The reaction is then allowed to occur for 37 minutes, and then final absorbance is read.

Volumes

| | BLANK (μl) | TOTAL (μl) | TEST (μl) |
|---|---|---|---|
| buffer | 200 | 150 | 100 |
| DAO | 50 | 50 | 50 |
| o-bzld | 50 | 50 | 50 |
| putrescine | 0 | 50 | 50 |
| compound | 0 | 0 | 50 |

D. Calculations

The initial absorbance value for each test and blank well serves as the blank for that well. This allows for correction of the optical density which may arise from any interfering absorbance arising from the compound. The initial absorbance for the blank well is used as an index to determine if the titration of any compound is acceptable if any highly abnormal pattern of absorbance is seen upon dilution of a test compound.

Values for the initial absorbance determinations are subtracted from the final absorbance values. The results are expressed as a percentage of the total enzyme activity in the absence of any test compound:

$TEST_{FINAL} - TEST_{INITIAL}/TOTAL_{FINAL} - TOTAL_{INITIAL})$
×100

A semi-logarithmic plot of concentration versus percent total will allow for calculating $IC_{50}$ values. Use of a software program such as INPLOT is recommended.

When representative compounds of this invention and aminoguanidine were tested in this assay, the following results were obtained:

| Test compound | $IC_{50}$ mM |
|---|---|
| N-(2-acetamidoethyl)hydrazine-carboximidamide hydrochloride | 6,858 |
| N-(3-acetamidopropyl)hydrazine-carboximidamide hydrochloride | 3,140 |
| Aminoguanidine hydrochloride | 21 |

EXAMPLE 9

To determine the effects of test compounds on the enzyme inducible nitric oxide synthase, and the resultant formation of nitric oxide, the following assay procedure is utilized.

Nitric oxide (NO) production by macrophage cells (RAW 264.7) is induced with lipopolysaccharride, and various test compounds are added to assess inhibition by the test compounds.

The cells are washed, counted and diluted to a concentration of $1.0 \times 10^6$ cells/ml. Then 100 ul cell/well are aliquoted to each well in a 96 well tissue culture plate to give a final concentraion of $1.0 \times 10^5$ cells/ml. The assay is set up in triplicate wells in order to harvest sufficient supernatant to be tested. The cells are incubated at 37° C. oven for two hours, and then the test compound added thereto. Incubation is continued for a further three hours at 37° C., after which the lipopolysaccharide is added. Incubation is then continued overnight at 37° C., and then, to a 300 μl sample is added 400 μl of 1% sulfanilamide in 4N HCl and 100 μl 6N HCl. This mixture is incubated for ten minutes at room temperature, and then 300 μl of 1% N-(1-napthyl) ethylenediamine dihydrochloride in methanol is added. The optical density is read after each addition at 540 nm.

When representative compounds of this invention and aminoguanidine were tested in this assay, the following results were obtained:

| Test compound | % inhibition of NO release |
|---|---|
| N-(2-acetamidoethyl)hydrazine-carboximidamide hydrobromide | 20 |
| N-(2-acetamidoethyl)hydrazine-carboximidamide hydrochloride | 15 |
| N-(3-acetamidopropyl)hydrazine-carboximidamide hydrochloride | 33 |
| Aminoguanidine hydrochloride | 44 |

EXAMPLE 10

| Tablet | mg/tablet |
|---|---|
| Compound of Formula I | 50 |
| Starch | 50 |
| Mannitol | 75 |
| Magnesium stearate | 2 |
| Stearic acid | 5 |

The compound, a portion of the starch and the lactose are combined and wet granulated with starch paste. The wet granulation is placed on trays and allowed to dry overnight at a temperature of 45° C. The dried granulation is comminuted in a comminutor to a particle size of approximately 20 mesh. Magnesium stearate, stearic acid and the balance of the starch are added and the entire mix blended prior to compression on a suitable tablet press. The tablets are compressed at a weight of 232 mg. using a 11/32" punch with a hardness of 4 kg. These tablets will disintegrate within a half hour according to the method described in USP XVI.

EXAMPLE 11

| Lotion | mg/g |
|---|---|
| Compound of Formula I | 1.0 |
| Ethyl alcohol | 400.0 |
| Polyethylene glycol 400 | 300.0 |
| Hydroxypropyl cellulose | 5.0 |
| Propylene glycol | to make 1.0 g |

EXAMPLE 12

To further study the ability of inhibitors of nonenzymatic browning to prevent the discoloration of protein on a surface, such as that which occurs on the tooth surface, the following surface browning experiment is performed. As a substitute for a pellicle-covered tooth surface, unexposed and developed photographic paper is used to provide a fixed protein (gelatin, i.e., collagen) surface on a paper backing. Five millimeter circles are punched and immersed for one week at 50° C. in a solution of 100 mM glucose-6-phosphate in a 0.5M phosphate buffer, pH 7.4, containing 3 mM sodium azide. Glucose-6-phosphate is a sugar capable of participating in nonenzymatic browning at a more rapid rate than glucose. In addition to the glucose-6-phosphate, chlorhexidine and/or a compound of Formula I are included. After incubation, the gelatin/paper disks are rinsed with water, observed for brown color, and photographed.

Incubation of the disks in glucose-6-phosphate alone shows slight brown color versus disks soaked in buffer alone. Inclusion of chlorhexidine (in the form of Peridex® at a final concentration of 0.04% chlorhexidine) shows significant browning. Addition of a compound of Formula I to the chlorhexidine completely inhibits browning of the gelatin, as does inclusion of a compound of Formula I in the absence of chlorhexidine.

The slight brown color formed by the action of glucose-6-phosphate on the gelatin surface alone and its prevention by a compound of Formula I demonstrates the utility of the present invention in preventing nonenzymatic browning of tooth surfaces. The enhanced browning in the presence of chlorhexidine and its prevention with a compound of Formula I demonstrates the utility of the present invention in preventing the anti-plaque agent-enhanced nonenzymatic browning which occurs with chlorhexidine.

EXAMPLE 13

| Oral Rinse | % |
|---|---|
| Compound of Formula I: | 1.4 |
| Chlorhexidine gluconate | 0.12 |
| Ethanol | 11.6 |
| Sodium saccharin | 0.15 |
| FD&C Blue No. 1 | 0.001 |
| Peppermint Oil | 0.5 |

-continued

| Oral Rinse | % |
| --- | --- |
| Glycerine | 10.0 |
| Tween 60 | 0.3 |
| Water to | 100 |

EXAMPLE 14

| Toothpaste | % |
| --- | --- |
| Compound of Formula I: | 5.5 |
| Sorbitol, 70% in water | 25 |
| Sodium saccharin | 0.15 |
| Sodium lauryl sulfate | 1.75 |
| Carbopol 934, 6% dispersion in | 15 |
| Oil of Spearmint | 1.0 |
| Sodium hydroxide, 50% in water | 0.76 |
| Dibasic calcium phosphate dihydrate | 45 |
| Water to | 100 |

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. A composition for inhibiting the advanced glycosylation of a target protein comprising an effective amount of a compound of the formula

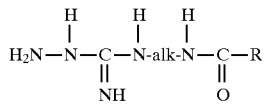

wherein alk is a straight or branched chain alkylene group containing from 2 to 8 carbon atoms, and R is a lower alkyl group containing from 1 to 6 carbon atoms; and their biologically or pharmaceutically acceptable acid addition salts, together with a carrier therefor.

2. The composition of claim 1 wherein R is a methyl group.

3. The composition of claim 1 which is N-(2-acetamidoethyl)hydrazinecarboximidamide hydrobromide, or another pharmaceutically acceptable salt thereof.

4. The composition of claim 1 which is N-(2-acetamidoethyl)hydrazinecarboximidamide hydrochloride, or another pharmaceutically acceptable salt thereof.

5. The composition of claim 1 which is N-(3-acetamidopropyl)hydrazinecarboximidamide hydrobromide, or another pharmaceutically acceptable salt thereof.

6. A pharmaceutical composition for administration to an animal to inhibit the advanced glycosylation of a target protein within said animal, comprising a pharmaceutically effective amount of a compound of the formula

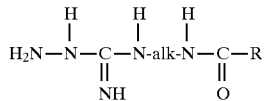

wherein alk is a straight or branched chain alkylene group containing from 2 to 8 carbon atoms, and R is a lower alkyl group containing from 1 to 6 carbon atoms; and their biologically or pharmaceutically acceptable acid addition salts, together with a carrier therefor.

7. The composition of claim 6 wherein R is a methyl group.

8. The composition of claim 6 which is N-(2-acetamidoethyl)hydrazinecarboximidamide hydrobromide, or another pharmaceutically acceptable salt thereof.

9. The composition of claim 6 which is N-(2-acetamidoethyl)hydrazinecarboximidamide hydrochloride, or another pharmaceutically acceptable salt thereof.

10. The composition of claim 6 which is N-(3-acetamidopropyl)hydrazinecarboximidamide hydrochloride, or another pharmaceutically acceptable salt thereof.

11. A method of inhibiting the formation of advanced glycosylation endproducts of a target protein, said method comprising administering an effective amount of a composition, said composition comprising a compound of the formula

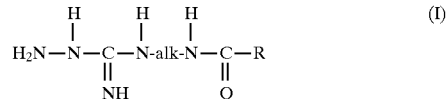

wherein alk is a straight or branched chain alkylene group containing from 2 to 8 carbon atoms, and R is a lower alkyl group containing from 1 to 6 carbon atoms; and their biologically or pharmaceutically acceptable acid addition salts, together with a carrier therefor.

12. The method of claim 11 wherein R is a methyl group.

13. The method of claim 11 wherein the compound of formula I is N-(2-acetamidoethyl)hydrazinecarboximidamide hydrobromide, or another pharmaceutically acceptable salt thereof.

14. The method of claim 11 wherein the compound of formula I is N-(2-acetamidoethyl)hydrazinecarboximidamide hydrochloride, or another pharmaceutically acceptable salt thereof.

15. The method of claim 11 wherein the compound of formula I is N-(3-acetamidopropyl)hydrazinecarboximidamide hydrochloride, or another pharmaceutically acceptable salt thereof.

16. A method for treating an animal to inhibit the formation of advanced glycosylation endproducts of a target protein within said animal, said method comprising administering an effective amount of a pharmaceutical composition, said pharmaceutical composition comprising a compound of the formula

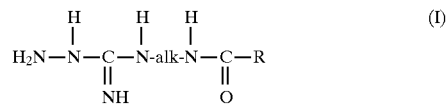

wherein alk is a straight or branched chain alkylene group containing from 2 to 8 carbon atoms, and R is a lower alkyl group containing from 1 to 6 carbon atoms; and their biologically or pharmaceutically acceptable acid addition salts, together with a carrier therefor.

17. The method of claim 16 wherein R is a methyl group.

18. The method of claim 16 wherein the compound of formula I is N-(2-acetamidoethyl)hydrazinecarboximidamide hydrobromide, or another pharmaceutically acceptable salt thereof.

19. The method of claim 16 wherein the compound of formula I is N-(2-acetamidoethyl)hydrazinecarboximidamide hydrochloride, or another pharmaceutically acceptable salt thereof.

20. The method of claim 16 wherein the compound of formula I is N-(3-acetamidopropyl)hydrazinecarboximidamide hydrochloride, or another pharmaceutically acceptable salt thereof.

21. A method of inhibiting the discoloration of teeth resulting from non-enzymatic browning in the oral cavity which comprises administration of an amount effective to inhibit the formation of advanced glycosylation endproducts of a composition comprising a compound of the formula

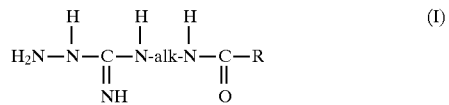   (I)

wherein alk is a straight or branched chain alkylene group containing from 2 to 8 carbon atoms, and R is a lower alkyl group containing from 1 to 6 carbon atoms; and their biologically or pharmaceutically acceptable acid addition salts, together with a carrier therefor.

22. A method for treating an animal to inhibit the formation of advanced glycosylation endproducts of a target protein within said animal, without concommitant effects upon the enzymes diaminooxidase and inducible nitric oxide synthase, said method comprising administering an effective amount of a pharmaceutical composition, said pharmaceutical composition comprising N-(2-acetamidoethyl)hydrazinecarboximidamide and its biologically or pharmaceutically acceptable acid addition salts, together with a carrier therefor.

23. The method of claim 22 wherein the composition comprises N-(2-acetamidoethyl)hydrazinecarboximidamide hydrobromide.

24. The method of claim 22 wherein the composition comprises N-(2-acetamidoethyl)hydrazinecarboximidamide hydrochloride.

25. The compound which is N-(2-acetamidoethyl)hydrazine-carboximidamide hydrobromide, or another pharmaceutically acceptable salt thereof.

26. The compound which is N-(2-acetamidoethyl)hydrazine-carboximidamide hydrochloride, or another pharmaceutically acceptable salt thereof.

* * * * *